United States Patent [19]

Sohda et al.

[11] Patent Number: 5,376,647
[45] Date of Patent: Dec. 27, 1994

[54] BISPHOSPHONIC ACID DERIVATIVES, AND USEFUL AS A BONE RESORPTION INHIBITOR

[75] Inventors: Takashi Sohda, Takatsuki; Iwao Yamazaki, Takarazuka; Noriaki Kawamura, Suita; Shigehisa Taketomi, Ikeda, all of Japan

[73] Assignee: Takeda Chemical Industries, Ltd., Japan

[21] Appl. No.: 3,955

[22] Filed: Jan. 19, 1993

Related U.S. Application Data

[63] Continuation of Ser. No. 718,648, Jun. 21, 1991, abandoned.

[30] Foreign Application Priority Data

| | | | |
|---|---|---|---|
| Jun. 25, 1990 | [JP] | Japan | 2-167600 |
| Dec. 12, 1990 | [JP] | Japan | 2-410501 |
| Apr. 23, 1991 | [JP] | Japan | 3-092080 |

[51] Int. Cl.⁵ .................. A61K 31/675; C07F 9/6524; C07F 9/6539
[52] U.S. Cl. ......................... 514/89; 546/24; 548/112; 548/118; 558/158
[58] Field of Search ............................ 546/24; 514/89

[56] References Cited

U.S. PATENT DOCUMENTS

| | | | |
|---|---|---|---|
| 4,096,208 | 6/1978 | Dursch et al. | 260/931 |
| 4,719,203 | 1/1988 | Bosies et al. | 514/108 |
| 4,746,654 | 5/1988 | Breliere et al. | 514/108 |
| 5,036,058 | 7/1991 | Jaeggi et al. | 514/86 |

FOREIGN PATENT DOCUMENTS

| | | | |
|---|---|---|---|
| 0151072 | 6/1985 | European Pat. Off. | 562/11 |
| 230068 | 7/1987 | European Pat. Off. | 514/86 |
| 243173 | 10/1987 | European Pat. Off. | 514/76 |
| 0282309 | 9/1988 | European Pat. Off. | 548/112 |
| 0282320 | 9/1988 | European Pat. Off. | 548/112 |
| 0298553 | 1/1989 | European Pat. Off. | 514/89 |
| 0325482 | 7/1989 | European Pat. Off. | 514/103 |
| 0337706 | 10/1989 | European Pat. Off. | 549/5 |
| 54-37829 | 3/1979 | Japan | 562/11 |
| 1258695 | 10/1989 | Japan | 548/112 |
| 445675 | 12/1972 | U.S.S.R. | 558/158 |

*Primary Examiner*—Alan L. Rotman
*Attorney, Agent, or Firm*—Wegner, Cantor, Mueller & Player

[57] ABSTRACT

A bisphosphonic acid derivative of the general formula (I):

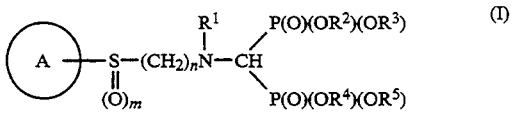

wherein A is an optionally substituted cyclic group; $R^1$ is hydrogen atom or a lower alkanoyl group; $R^2$, $R^3$, $R^4$ and $R^5$ are the same or different and are hydrogen atom or a lower alkyl group; m is 0, 1 or 2; and n is an integer from 2 to 10, or a salt thereof is disclosed. A process for its production and a bone resorption inhibitor containing the compound of the general formula (I) or a salt thereof are also disclosed.

7 Claims, No Drawings

BISPHOSPHONIC ACID DERIVATIVES, AND USEFUL AS A BONE RESORPTION INHIBITOR

This application is a continuation of U.S. application Ser. No. 07/718,648 filed Jun. 21, 1991, now abandoned.

FIELD OF THE INVENTION

The present invention relates to (sulfur-containing alkyl)aminomethylenebisphosphonic acid derivatives or pharmaceutically acceptable salts thereof which are useful as medicament having bone resorption inhibitory activity as well as anti-inflammatory activity, antirheumatic activity and the like, and a medicament containing the compounds as an active component.

PRIOR ART

Various aminomethylenebisphosphonic acid derivatives have been synthesized as disclosed in Japanese Patent Laid Open Publication Nos. 308290/1989, 258695/1990, 184/1990, 185/1990 and the like. However, none of them discloses (sulfur-containing alkyl)aminomethylenebisphosphonic acid derivatives of the present invention.

OBJECTS OF THE INVENTION

Although various bisphosphonic acid derivatives have been produced as bone resorption inhibitors, they are yet insufficient from the viewpoint of their activity and side effects.

In view of these circumstances, the present inventors have studied intensively to develop bisphosphonic acid derivatives which are more useful as bone resorption inhibitors. As a result, it has been found that novel bisphosphonic acid derivatives of the general formula (I) as shown hereinafter can directly effect bone to manifest excellent bone resorption inhibitory activity.

SUMMARY OF THE INVENTION

The compound of the present invention is characterized by its chemical structure in that it has thio, sulfinyl or sulfonyl group bound to a cyclic group on the alkyl side-chain, and the compounds of the present invention can be used as bone resorption inhibitors.

Namely, according to the present invention, there is provided, (1) a bisphosphonic acid derivative of the general formula (I):

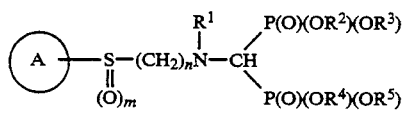

wherein A is an optionally substituted cyclic group; $R^1$ is hydrogen atom or a lower alkanoyl group; $R^2$, $R^3$, $R^4$ and $R^5$ are the same or different and are hydrogen atom or a lower alkyl group; m is 0, 1 or 2; and n is an integer from 2 to 10, or a salt thereof, (2) a process for production of the compound of the general formula (I) which comprises reacting an amine derivative of the general formula (II):

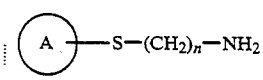

wherein all the symbols are as defined above, with an orthoformate derivative of the general formula (III):

wherein $R^6$ is a lower alkyl group, and a phosphite derivative of the general formula (IV):

wherein $R^7$, $R^8$, $R^9$ and $R^{10}$ are the same or different and are a lower alkyl group, and then optionally subjecting the resultant to acylation, oxidation and/or hydrolysis, and (3) a bone resorption inhibitor which comprises the compound of the general formula (I) or a salt thereof.

DETAILED DISCLOSURE OF THE INVENTION

In the above general formula (I), the optionally substituted cyclic group represented by A includes $C_{6-14}$ aromatic hydrocarbon residues such as phenyl, naphthyl, anthryl and the like; 5 or 6-membered aromatic heterocyclic groups containing 1 to 4 hetero atoms, preferably, nitrogen, oxygen and/or sulfur atoms (e.g., pyridyl, pyrimidinyl, pyridazinyl, furyl, thienyl, imidazolyl, thiazolyl, oxazolyl isoxazolyl, thiadiazolyl, pyrazolyl, triazolyl, etc.); 5 or 6 membered aromatic heterocyclic groups containing 1 to 4 nitrogen, oxygen and/or sulfur atoms which are conjugated with a $C_{6-14}$ aromatic hydrocarbon ring or with a 5 or 6 membered aromatic heterocyclic ring containing 1 to 4 nitrogen, oxygen and/or sulfur atoms (e.g., benzothiazolyl, benzoxazolyl, benzoimidazolyl, s-triazolo[1,2-a]pyridyl, imidazo[1,2-b]pyrazinyl, indolyl, imidazo[1,2-a]pyridyl, etc.); $C_{3-7}$ cyclic alkyl groups such as cyclopropyl, cyclobutyl, cyclopentyl, cyclohexyl, cycloheptyl and the like; and 5 or 6-membered non-aromatic heterocyclic group containing 1 to 4 hetero atoms, preferably, nitrogen, oxygen and/or sulfur atoms (e.g., thiazolin-2-yl, imidazolin-2-yl, oxazolin-2-yl, etc.). When a cyclic group containing nitrogen atom as the hetero atom has a substituent, such a substituent may attach to either the carbon atom or nitrogen atom in the cyclic group.

In the above general formula (I), examples of the substituent of the ring A include a halogen atom, nitro group, an optionally substituted alkyl group, optionally substituted hydroxyl group, optionally substituted thiol group. These substituents may be the same or different and the ring A may have 1 to 4, preferably 1 or 2 substituents.

The term "halogen atom" used herein includes fluorine, chlorine, bromine, iodine and the like. The alkyl group in the optionally substituted alkyl group is preferably, a $C_{1-7}$ straight or branched chain alkyl group such as methyl, ethyl, propyl, isopropyl, butyl, isobutyl, sec-butyl, tert-butyl, pentyl, isopentyl, neopentyl, hexyl or heptyl or the like; or a $C_{3-7}$ cycloalkyl group such as cyclopropyl, cyclobutyl, cyclopentyl, cyclohexyl, cycloheptyl or the like. They may be substituted with 1 to 3 substituents such as a halogen atom (e.g., fluorine, chlorine, bromine, iodine, etc.), hydroxyl group, a $C_{1-6}$ alkoxy group (e.g., methoxy, ethoxy, propoxy, butoxy, hexyloxy, etc.) and the like.

The examples of the substituted alkyl group include trifluoromethyl, 2,2,2-trifluoroethyl, trichloromethyl, hydroxymethyl, 2-hydroxyethyl, 2-methoxyethyl and the like.

The substituted hydroxyl group is that having a suitable substituent, particularly, a protecting group for a hydroxyl group, for example, alkoxy, alkenyloxy, aralkyloxy, acyloxy as well as aryloxy. Examples of the alkoxy group include $C_{1-6}$ straight or branched chain alkoxy groups (e.g., methoxy, ethoxy, propoxy, isopropoxy, butoxy, isobutoxy, sec-butoxy, tert-butoxy, pentoxy, isopentoxy, neopentoxy, hexyloxy, etc.) and $C_{4-6}$ cycloalkoxy groups (e.g., cyclobutoxy, cyclopentoxy, cyclohexyloxy, etc.) and examples of the alkenyloxy group preferably include $C_{2-6}$ alkenyloxy groups such as allyloxy, crotyloxy, 2-pentenyloxy, 3-hexenyloxy, 2-cyclopentenylmethoxy and the like. As the aralkyloxy group, preferably, $C_{6-19}$ aralkyloxy groups, more preferably, $C_{6-14}$ aryl-$C_{1-4}$ alkyloxy groups (e.g., benzyloxy, phenethyloxy, etc.) may be used. As the acyloxy group, preferably, alkanoyloxy groups, for example, $C_{2-7}$ alkanoyloxy groups (e.g., acetyloxy, propionyloxy, n-butyryloxy, iso-butyryloxy, hexanoyloxy, etc.) may be used. As the aryloxy group, preferably, $C_{6-14}$ aryloxy groups (e.g., phenoxy, biphenyloxy, etc.) may be used. These groups may be further substituted with 1 to 3 substituents such as the above-described halogen atom, hydroxyl group, $C_{1-6}$ alkoxy group and the like. Examples of the substituted hydroxyl group include trifluromethoxy, difluoromethoxy, 2,2,2-trifluoroethoxy, 2-methoxyethoxy, 4-chlorobenzyloxy, 2-(3,4-dimethoxyphenyl)ethoxy and the like.

The substituted thiol group is a thiol group having a suitable substituent, particularly, a protecting group for thiol group, for example, alkylthio, aralkylthio, acylthio. As the alkylthio group, preferably a $C_{1-6}$ straight or branched chain alkylthio group (e.g., methylthio, ethylthio, propylthio, isopropylthio, butylthio, isobutylthio, sec-butylthio, tert-butylthio, pentylthio, isopentythio, neopentylthio, hexylthio, etc.), and a $C_{4-7}$ cycloalkylthio (e.g., cyclobutylthio, cyclopentylthio, cyclohexylthio, cycloheptylthio, etc.) may be used. As the aralkylthio group, preferably, a $C_{7-19}$ aralkylthio group, more preferably a $C_{6-14}$ aryl-$C_{1-4}$ alkylthio group such as benzylthio or phenetylthio may be used. As the acylthio group, preferably, alkanoylthio group such as $C_{2-7}$ alkanoylthio (e.g., acetylthio, propionylthio, n-butyrylthio, iso-butyrylthio, hexanoylthio, etc.) may be used. These groups may be further substituted with, for example, 1 to 3 substituents such as the above-described halogen atom, hydroxyl group, $C_{1-6}$ alkoxy group and the like. Examples of the substituted thiol group include trifluoromethylthio, difluoromethylthio, 2,2-trifluoroethylthio, 2-methoxyethylthio, 4-chlorobenzylthio, 3,4-dichlorobenzylthio, 4-fluorobenzylthio, 2-(3,4-dimethoxyphenyl)ethylthio and the like.

Examples of the substituted aromatic hydrocarbon group include 4-chlorophenyl, 2-fluorophenyl, 4-nitrophenyl, 3-methylphenyl, 3-trifluoromethylphenyl, 5,6,7,8-tetrahydro-2-naphthyl, 4-methoxyphenyl, 3,4-methylenedioxyphenyl, 4-(4-chlorbenzyloxy)phenyl, 4-acetoxyphenyl, 3-methylthiophenyl and the like.

Examples of the substituted aromatic heterocyclic group include 2-chloro-4-pyridyl, 5-nitro-2-pyridyl, 3-hydroxy-2-pyridyl, 6-methoxy-2-pyridyl, 2-methyl-4-pyridyl, 4-methyl-2-pyrimidinyl, 4-hydroxy-6-methyl-2-pyrimidinyl, 5-trifluoromethyl-2-benzothiazolyl and the like.

Examples of the substituted heterocyclic group include 5-phenyl-2-thiazolin-2-yl, 5-methyl-2-oxazoiin-2-yl, 1-methyl-2-imidazolin-2-yl and the like.

As the lower alkanoyl group represented by $R^1$, $C_{1-6}$ alkyl-carbonyl group (e.g., acetyl, propionyl, butyryl, isobutyryl, valeryl, isovaleryl, pivaloyl, hexanoyl, cyclopentanecarbonyl, etc.) may be used. Preferably, $R^1$ is, for example, acetyl, propionyl, butyryl or the like.

The lower alkyl group represented by $R^2$, $R^3$, $R^4$ and $R^5$ include $C_{1-4}$ straight or branched chain alkyl groups, for example, methyl, ethyl, propyl, butyl, isopropyl, isobutyl, tert-butyl and the like.

Among the above groups, the ring A is preferably benzene ring, pyridine ring or pyrimidine ring which may be substituted with a halogen atom, an alkyl group or an alkoxy group.

The suitable salts of the compound (I) are pharmaceutically acceptable salts, for example, inorganic salts such as alkali metal salts (e.g., sodium salt, potassium salt, etc.), alkaline earth metal salts (e.g., calcium salt, magnesium salt, etc.) or ammonium salt; salts with organic bases such as methylamine salt, ethylamine salt, propylamine salt, isopropylamine salt, butylamine salt, tert-butylamine salt, dimethylamine salt, diethylamine salt, trimethylamine salt, triethylamine salt, pyridine salt, picoline salt, dicyclohexylamine salt, N,N'-dibenzylethylenediamine salt and the like; organic acid salts such as formate, acetate, trifluoroacetate, maleate, tartrate, methanesulfonate, benzenesulfonate, toluenesulfonate and the like; inorganic acid salts such as hydrochloride, hydrobromide, sulfonate and the like; and salts with amino acids such as lysine, glutamic acid and the like.

The compound (I) or a salt thereof can be produced by the known methods.

Namely, the compound (I) or its salt can be produced by reacting an amine derivative of the general formula (II):

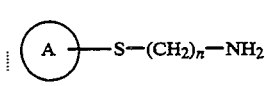
(II)

wherein A is an optionally substituted cyclic group; and n is an integer of 2 to 10, with an orthoformate derivative of the general formula (III):

(III)

wherein $R^6$ is a lower alkyl group, and a phosphite derivative of the general formula (IV):

(IV)

wherein $R^7$, $R^8$, $R^9$ and $R^{10}$ are the same or different and are a lower alkyl group, and then optionally subjecting the resultant to acylation, oxidation and/or hydrolysis.

For example, the compound (I) or a salt thereof can be produced by the following methods. The salts of the compounds described hereinafter may be the same as those described with respect to the compound (I).

Method A

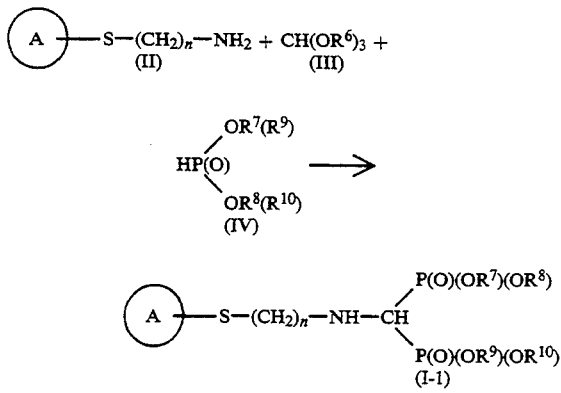

wherein all the symbols are as defined above.

Method B

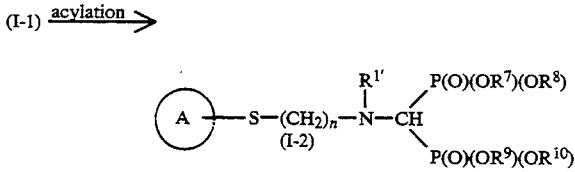

wherein $R^{1'}$ represents a lower acyl group, and the other symbols are as defined above.

Method C

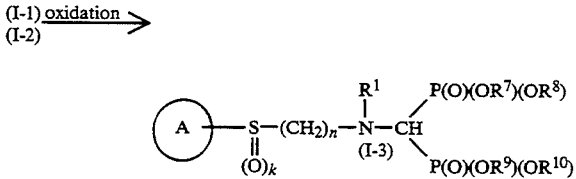

wherein k represents 1 or 2, and the other symbols are as defined above.

Method D-1

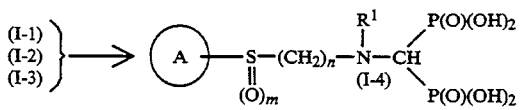

wherein all the symbols are as defined above.
Method D-2
The production of a bisphosphonic acid diester.
Method D-3
The production of a bisphosphonic acid mono- or triester.
Each method is illustrated in detail below.
Method A This method produces the bisphosphonate derivative (I-1) by reacting the amine derivative (II) with the orthoformate derivative (III) and the phosphite derivative (IV) in amounts suitable for the reaction. The reaction is usually conducted at 80° C. to 200° C., preferably at 100° C. to 170° C. for 10 minutes to 24 hours.
Method B In this method, the compound (I-2) is produced by acylation of the compound (1-I) produced by the method A. This acylation is conducted by reacting the compound (1-I) with 1 to 2 equivalents of an acylating agent (acid anhydride, acid halide, etc.) in a solvent or without any solvent. As the solvent, benzene, xylene, toluene, chloroform, dichloromethane, ethyl acetate, ether, tetrahydrofuran or the like may be used. The reaction is conducted at 0° C. to 100° C. for 30 minutes to 10 hours.
Method C This method is conducted by oxidation using an oxidizing agent according to the conventional method. Such an oxidizing agent is a mild one which produces less substantial effect on the skeleton of the sulfur-containing heterocyclic compound, and preferably, m-chloroperbenzoic acid, hydrogen peroxide, peresters, sodium metaperiodate or the like may be used.

This reaction is conducted in an organic solvent which has no adverse effect on the reaction.

As the solvent, for example, a halogenated hydrocarbon (e.g., methylene chloride, chloroform, dichloroethane, etc.), or hydrocarbon (e.g., benzene, toluene, etc. ) or a mixed solvent thereof may be used.

When equimolar or less of the oxidizing agent is used based on the compound (I-1) or (I-2), the compound (I-3) wherein k is 1 is preferentially produced. When more than equimolar amount of the oxidizing agent is used, the compound (I-3) wherein k is 1 is further oxidized to produce the compound (I-3) wherein k is 2.

This reaction proceeds at a temperature of not higher than room temperature (20° C. to 30° C.). Preferably, the reaction temperature is between about −50° C. to 20° C.

The reaction time is from 30 minutes to 10 hours.
Method D-1

In this method, the bisphosphonates (i-1), (I-2) and (I-3) produced by the above methods A to C are subjected to hydrolysis to produce the corresponding bisphosphonic acid (I-4).

This reaction is conducted using an inorganic acid such as hydrochloric acid, hydrobromic acid or the like or a halogenated trialkylsilane in a solvent which has no adverse effect on the reaction. When an inorganic acid such as hydrochloric acid, hydrobromic acid or the like is used, an alcohol such as methanol, ethanol, 2-methoxyethanol, ethylene glycol, propanol, butanol or th like, water or a mixed-solvent thereof is used as the solvent. The amount of the acid used is usually large excess and the reaction temperature is 0° C. to 150° C., preferably 30° C. to 100° C., and the reaction time is 1 to 50 hours.

When a halogenated alkylsilane such as chlorotrimethylsilane, bromotrimethylsilane, iodotrimethylsilane or the like is used, a halogenated hydrocarbon such as carbon tetrachloride, chloroform, dichloromethane, 1,2-dichloroethane, 1,1,2,2-tetrachloroetahne, acetonitrile or the like or a mixed solvent thereof may be used as the solvent.

The amount of the halogenated alkylsilane used is 4 to 10 equivalent, preferably 5 to 8 equivalent of the compound (I-1), (I-2) or (I-3). The reaction temperature is −30° C. to 100° C., preferably −10° C. to 50° C. and the reaction time is 30 minutes to 100 hours.

In order to convert the bisphosphonic acid thus obtained into a salt thereof, the acid is treated according to the conventional method using a base such as potassium hydroxide, sodium hydroxide, sodium methoxide, ammonia, organic amines or the like.

Method D-2

In this method, the bisphosphonic acid tetraester (I-4) produced by the method A is subjected to hydrolysis with a base to produce the bisphosphonic acid diester.

The amount of the base (e.g., sodium hydroxide, potassium hydroxide, etc.) to be used is 2 to 2.2 molar equivalent based on the compound (I-1) and the reaction is conducted in a solvent containing water according to the conventional method.

Method D-3

In this method, the bisphosphonic acid tetraesters (I-1), (I-2) and (I-3) produced by the methods A to C are subjected to partial hydrolysis with a halogenated alkylsilane to produce the bisphosphonic acid tetraesters.

The amount of the halogenated alkylsilicon (e.g., chlorotrimethylsilane, bromotrimethylsilane, iodotrimethylsilane, etc.) to be used is 1 to 1.2 molar equivalent based on the compound (I-1), (I-2) or (I-3) in the case of the triester production, and 3 to 3.3 molar equivalent based on the compound in the case of the monoester production, and the reaction is conducted according to the method D-1.

The bisphosphonic acid derivative (I) thus obtained can be isolated and purified according to known means for separation and purification, for example, by concentration, concentration under reduced pressure, solvent extraction, precipitation, recrystallization, chromatography and the like.

The starting compound (II) of the present invention can be produced, for example, by the following method.

Method E

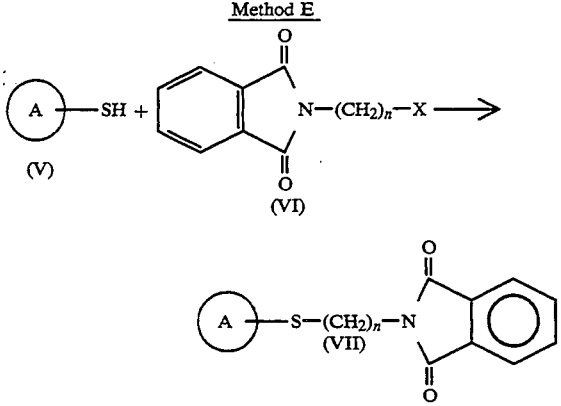

wherein the ring A and n are as defined above, and X represents a leaving group.

In this method, the compound (V) is reacted with the compound (VI) in the presence of a base to produce the compound (VII). The leaving group represented by X is, for example, a halogen, preferably chlorine, bromine or iodine, or an activated hydroxyl group, for example, an esterified organic sulfonic acid residue (e.g., p-toluenensulfonyloxy group, etc.), a $C_{1-4}$ alkylsulfonyloxy group (e.g., methanesulfonyloxy group, etc.) or an esterified organic phosphoric acid residues such as diphenylphosphoryloxy group, dibenzylphosphoryloxy group, dimethylphosphoryloxy group and the like. The reaction of the compounds (V) with (VI) is conducted in a suitable solvent. Examples of the solvent include aromatic hydrocarbons such as benzene, toluene, xylene; ethers such as dioxane, tetrahydrofuran, dimethoxyethane; alcohols such as methanol, ethanol, propanol; ethyl acetate; acetonitrile; pyridine; N,N-dimethylformamide; dimethylsulfoxide; chloroform; dichloromethane; 1,2-dichloroethane; 1,1,2,2-tetrachloroethane; acetone; 2-butanone and a mixed solvent thereof. The reaction of the compounds (V) with (VI) is conducted in the presence of a suitable base, for example, an alkali metal salt such as sodium hydroxide, potassium hydroxide, potassium carbonate, sodium carbonate, sodium bicarbionate or the like; or an amine such as pyridine, N,N-dimethylaniline or the like. The amount of the base to be used is preferably about 1 to 5 moles based on the compound (V). This reaction is usually conducted at −20° C. to 150° C., preferably about 0° C. to 130° C. for 1 to 10 hours.

Method F

First step reaction:

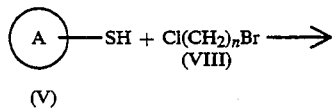

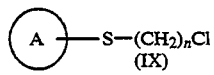

wherein the ring A and n are as defined above.

In this method, the compound (V) is firstly reacted with about equimolar amount of the compound (VIII) in the presence of a base to produce the compound (IX). The reaction between the compounds (V) and (VIII) is conducted in the same manner as that of Method E.

Second step reaction:

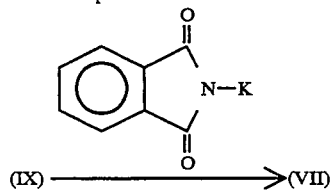

wherein the ring A and n are as defined above.

In this method, the compound (IX) obtained in the first step of Method F is reacted with about equimolar amount of potassium phthalimide to produce the compound (VII). The reaction between the compound (IX) and potassium phthalimide is conducted in a suitable solvent. Examples of the solvent include aromatic hydrocarbons such as benzene, toluene, xylene and the like; ethers such as dioxane, tetrahydrofuran, dimethoxyethane and the like; alcohols such as methanol, ethanol, propanol and the like; ethyl acetate; acetonitrile; pyridine; N,N-dimethylformamide; dimethylsulfoxide; chloroform; dichloromethane; 1,2-dichtoroethane; 1,1,2,2-tetrachloroethane; acetone; 2-butanone and a mixed solvent thereof. This reaction is usually conducted at −20° C. to 150° C., preferably about 30° C. to 130° C. for 1 to 10 hours.

Method G

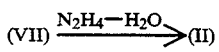

wherein the ring A and n are as defined above.

In this method, the compound (VII) prepared by the methods E and F is reacted with hydrazine hydrate to produce the compound represented by the general formula (II). The reaction between the compound (VII) and hydrazine hydrate is conducted in a suitable solvent. Examples of the solvent include aromatic hydrocarbons such as benzene, toluene, xylene and the like; ethers such as dioxane, tetrahydrofuran, dimethoxyethane and the like; alcohols such as methanol, ethanol, propanol and the l i ke; N,N-dimethylformamide; dimethylsulfoxide; chloroform; dichloromethane; 1,2-dichloroethane; 1,1,2,2-tetrachloroethane and a mixed solvent thereof. The amount of the hydrazine hydrate used is 1 to 10 molar equivalent, preferably, 1.2 to 5 molar equivalent based on the compound (VII). This reaction is usually conducted at −20° C. to 150° C., preferably about 0° C. to 100° C. for 1 to 10 hours.

The compound (I) or a salt thereof provided by the present invention has bone resorption inhibitory activity and prevent bone loss caused by bone resorption.

Accordingly, the compound of the present invention can be used for prevention or treatment of osteoporosis of mammals (e.g., mouse, rat, rabbit, dog, cat, cattle, pig, man, etc.).

When the compound of the present invention is administered to man, it can be administered by way of either oral or parenteral route. A composition for oral administration may be a solid or liquid dosage forth, for example, tablets (including sugar coated tablets, film coated tablets ), pills, granules, powder, capsules (including soft capsules), syrup, emulsion, suspension and the like. Such compositions can be prepared by known methods and may contain a carrier or excipient which is conventionally used in the field of pharmaceutical preparations. For example, a carrier or excipient for tablets includes lactose, starch, sucrose, magnesium stearate and the like.

The composition for parenteral administration may be an injection preparation or suppository, and such an injection preparation includes dosage forms for subcutaneous injection, intracutaneous injection, intramuscuiar injection and the like. The injection preparation can be prepared by a known method, namely, by a method wherein the compound (i) is suspended or emulsified in a sterilized aqueous or oily solution which is usually used for injection preparations. Such an aqueous solution for injection includes physiological saline, isotonic solution and the like. If desired, the solution may be used in a combination with a suitable suspending agent, for example, sodium carboxymethylcellulose, a nonionic surfactant or the like. The oily solution includes sesame oil, soybean oil and the like, and may be used in a combination with a solubilizing agent such as benzyl benzoate, benzyl alcohol, or the like. The injection preparation thus obtained is usually filled in a suitable ampoule.

When the compound (I) or a salt thereof is used as medicine for treatment of osteoporosis, the daily dosage for an adult is 1 to 500 mg, preferably 10 to 200 mg in the case of oral administration.

The method for measurement of bone resorption inhibitory activity and effect of osteoporosis treatment of the compound (I) as well as the result thereof are set forth below.

Bone resorption inhibitory activity

Measurement of bone resorption inhibitory activity was conducted according to Raisz's method [J. Clin. Invest., 44, 103–116 (1965)]. Namely, a rat (Sprague-Dawley, 19th day of pregnancy) was subcutaneously injected with 50 μCi $^{45}Ca$ (calcium isotope, $CaCl_2$ solution) and subjected to abdominal incision on the next day to aseptically remove fetal rats. Both cubital bones (radius, cubitus) were cut off under anatomic microscopic observations and the connective tissue and cartilage were removed as much as possible to obtain a sample for a bone culture. Each piece of the bones was cultivated in 0.6 ml $BGJ_b$ medium (Fitton-Jackson modification [GIBCO Laboratories (U.S.A.)] containing 2 mg/ml of bovine serum albumin) at 37° C. for 24 hours, and then the compound to be tested was added so that the concentration thereof became 10 μg/ml. Then, the cultivation was further continued in the above medium for 2 days, and the radioactivity of $^{45}Ca$ in the medium and that in the bone were measured. The amount (%) of $^{45}Ca$ released in the medium from the bone was calculated by the following equation.

Ratio of $^{45}Ca$ released in medium from bone (%) =

$$\frac{\text{Count of }^{45}Ca\text{ in medium}}{\text{Count of }^{45}Ca\text{ in medium + Count of }^{45}Ca\text{ in bone}} \times 100$$

The bone obtained from the litter fetus and cultivated according to the same manner without addition of a compound to be tested for 2 days was used as a control group. The average value±standard deviation of the data obtained from five bones of each group was calculated. The ratio (%) of the value thus obtained to that of the control group was obtained and shown in Table 1.

TABLE 1

| Ex. No. | Release of $Ca^{45}$ (%, to the control group) |
|---|---|
| 5 | 73 |

Effect on treatment of osteoporosis

The both ovaries of a SAM-R/1 mouse (13-weeks old) were removed and a test compound was orally administered to the animal for 6 days per one week, totally for 17 days in 3 weeks from the next day of the operation. On the next day of the last administration, the left femur of the mouse was removed. Trochlea was removed from the femur, and then the distal one-third of the femur was cut at right angles to the longitudinal axis. The bone-marrow was removed by dissolving with 0.2N aqueous potassium hydroxide, and placed in a glass tube. It was placed in an electric dryer and dried at 100° C. for 3 hours, then dry weight was measured.

The average value±standard deviation of the data obtained from the measurement of 6 to 8 mice per group are shown in Table 2.

TABLE 2

| Group | Daily Dose (mg/kg) | Weight (Dry Basis) (mg) |
|---|---|---|
| Sham operation control group | 0 | 10.18 ±0.18** |
| Ovary removed | 0 | 9.16 |

TABLE 2-continued

| Group | Daily Dose (mg/kg) | Weight (Dry Basis) (mg) |
|---|---|---|
| control group | | ±0.09 |
| Ovary removed | 30 | 10.31 |
| compound (Ex. 5) administered | | ±0.31** |

Significance with respect to the ovary removed control group
*: $p < 0.05$, **: $p < 0.01$ Effect on prevention and treatment of osteoporosis A male Sprague-Dawley rat (6-weeks old) was administered with the specimen (the compound) intraperitoneally for 2 days, and on the third day, the right sciatic nerve of the rat was cut out. Both cnemis were removed on the 17th day. The proximal half portion of the cnemis was cut out at right angles to the longitudinal axis and then dried at 110° C. for 6 hours. The dry weight was measured.

The average value±standard deviation obtained from of the data from the measurement of 6 mice per group are shown in Tables 3 and 4.

TABLE 3

| Group | Daily Dose (mg/kg) | Weight (Dry Basis) (mg) Right cnemis | Left cnemis |
|---|---|---|---|
| Sham operation control group | 0 | 99.8 ± 3.9** | 109.7 ± 1.5 |
| Operation control group | 0 | 79.4 ± 2.1 | 106.7 ± 1.1 |
| Operation compound (Ex. 10) administered group | 1 | 146.8 ± 5.8** | 157.0 ± 6.6** |

Significance with respect to the operation control group
**: $p < 0.01$

TABLE 4

| Group | Daily Dose (mg/kg) | Weight (Dry Basis) (mg) Right cnemis | Left cnemis |
|---|---|---|---|
| Sham operation control group | 0 | 98.1 ± 3.5** | 97.5 ± 0.6 |
| Operation control group | 0 | 77.3 ± 1.7 | 99.6 ± 2.4 |
| Operation compound (Ex. 41) administered group | 1 | 134.4 ± 4.5** | 143.7 ± 5.2** |

Significance with respect to the operation control group
**: $p < 0.01$

The following Reference Examples and Examples further illustrate the present invention in detail but are not to be construed to limit the scope thereof.

Reference Example 1

A mixture of 2-mercaptopyrimidine (7.3 g), N-(2-bromoethyl)phthalimide (16.5 g), potassium carbonate (10.8 g) and N,N-dimethylformamide (DMF) (85 ml) was stirred at room temperature for 3 hours. The reaction mixture was poured into water and the crystals separated were collected by filtration to obtain N-[2-(2-pyrimidinylthio)ethyl]-phthalimide (17.3 g, 93%). The resultant was recrystallized from ethanol-isopropyl ether to obtain pale yellow prisms, m.p. 149°–150° C.

Reference Examples 2 to 20

According to the same manner as that described in Reference Example 1, the compounds shown in Tables 5 and 6 were obtained.

TABLE 5

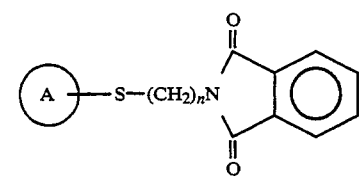

| Ref. Ex. | A | n | Yield (%) | m.p. (°C.) | Recrystn. solvent |
|---|---|---|---|---|---|
| 2 | phenyl | 2 | 78 | 53-54 | ether-hexane |
| 3 | phenyl | 3 | 88 | 83-84 | isopropyl ether |
| 4 | phenyl | 4 | 83 | 65-66 | isopropyl ether |
| 5 | 4-chlorophenyl | 4 | 85 | 84-85 | isopropyl ether |
| 6 | 2-pyridyl | 2 | 90 | 98-99 | isopropyl ether |
| 7 | 2-pyridyl | 3 | 88 | 103-104 | acetone-isopropyl ether |
| 8 | 2-pyridyl | 4 | 99 | crude*1) oil | — |
| 9 | 2-pyrazinyl | 2 | 88 | 147-148 | ethyl acetate |
| 10 | 2-pyrazinyl | 3 | 90 | 131-132 | ethyl acetate |
| 11 | 2-pyrazinyl | 4 | 94 | 105-106 | isopropyl ether |

TABLE 5-continued

A—S—(CH₂)ₙN(phthalimide)

| Ref. Ex. | A | n | Yield (%) | m.p. (°C.) | Recrystn. solvent |
|---|---|---|---|---|---|
| 12 | (1-methyl-imidazol-2-yl) | 2 | 76 | 108–109 | ethyl acetate hexane |

TABLE 6

A—S—(CH₂)ₙN(phthalimide)

| Ref. Ex. | A | n | Yield (%) | m.p. (°C.) | Recrystn. solvent |
|---|---|---|---|---|---|
| 13 | (1-methyl-imidazol-2-yl) | 4 | 89 | 43–45 | isopropyl ether-hexane |
| 14 | (5-methyl-1,3,4-thiadiazol-2-yl) | 2 | 92 | 127–128 | ethanol |
| 15 | (5-methyl-1,3,4-thiadiazol-2-yl) | 4 | 98 | 100–101 | ethanol |
| 16 | (pyrimidin-2-yl) | 3 | 85 | 95–96 | ethanol-isopropyl ether |
| 17 | (pyrimidin-2-yl) | 4 | 98 | 100–101 | ethyl acetate-hexane |
| 18 | (2-pyridyl N-oxide) | 4 | 78 | 174–176 | ethyl acetate |

TABLE 6-continued

A—S—(CH₂)ₙN(phthalimide)

| Ref. Ex. | A | n | Yield (%) | m.p. (°C.) | Recrystn. solvent |
|---|---|---|---|---|---|
| 19 | (thiazol-2-yl) | 4 | 97 | 84–85 | ethyl acetate-hexane |
| 20 | (imidazo[1,2-a]pyridin-2-yl)*¹⁾ | 4 | 73 | 127–128 | ethyl acetate |

*¹⁾NMR(δppm CDCl₃): 1.7–1.95(4H, m), 3.22(2H, t, J=7Hz), 3.73(2H, t, J=7Hz), 6.96(1H, ddd, J=7, 5,1Hz), 7.15(1H, ddd, J=8.1, 1Hz), 7.46(1H, ddd, J=8, 7, 2Hz), 7.7–7.75(2H, m), 7.8–7.85(2H, m), 8.40(1H, ddd, J=5, 2, 1Hz).

Reference Example 21

A mixture of 1-bromo-5-chloropentane (10.0 g), thiophenol (5.94 g), potassium carbonate (7.45 g) and N,N-dimethylformamide (DMF) (50 ml) was stirred at room temperature for 4 hours. The reaction mixture was poured into water and extracted with ethyl acetate. The ethyl acetate layer was washed with water, dried (MgSO₄), and then concentrated to dryness. Potassium phthalimide (11.0 g) and N,N-dimethylformamide (100 ml) were added to the residue and the resultant was stirred at 90° C. for 2 hours. The reaction mixture was poured into water and the mixture was extracted with ethyl acetate. The ethyl acetate layer was washed with water, dried (MgSO₄), and then concentrated to dryness. The crystals were collected by filtration and recrystallized from isopropyl ether to obtain N-(5-phenylthiopentyl)phthalimide (14.9 g, 85%) as colorless prisms, m.p. 87°–88° C.

Reference Examples 22 to 26

According to the same manner as that described in Reference Example 21, the compounds shown in Table 7 were obtained.

TABLE 7

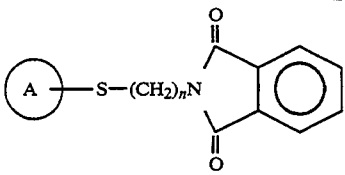

| Ref. Ex. | A— | n | Yield (%) | m.p. (°C.) | Recrystn, solvent |
|---|---|---|---|---|---|
| 22 | phenyl | 6 | 91 | 51–52 | isopropyl ether-hexane |
| 23 | 2-pyridyl | 5 | 73 | 64–65 | isopropyl ether |
| 24 | 2-pyridyl | 6 | 91 | crude[1] oil | — |
| 25 | 4-pyridyl | 5 | 79 | 90–91 | ethyl acetate-hexane |

TABLE 7-continued

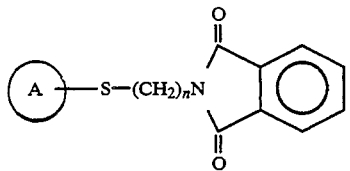

| Ref. Ex. | A— | n | Yield (%) | m.p. (°C.) | Recrystn, solvent |
|---|---|---|---|---|---|
| 26 | 2-pyrimidinyl | 5 | 87 | 95–96 | ethyl acetate-hexane |

[1]NMR(δppm in CDCl$_3$):1.25–1.8(8H, m), 3.15(2H, t, J=7Hz), 3.68 (2H, t, J=7Hz), 6.95(1H, ddd, J=7, 5, 1Hz), 7.15(1H, ddd, J=8, 1, 1Hz), 7.46(1H, ddd, J=8, 7, 2Hz), 7.65–7.75(2H, m), 7.8–7.9(2H, m), 8.41(1H, ddd, J=5, 2, 1Hz).

Reference Example 27

A mixture of N-[2-(2-pyrimidinylthio)ethyl]phthalimide (17.1 g), hydrazine hydrate (21 g) and ethanol (200 ml) was stirred for one hour under reflux. The crystals separated was filtered off, and the filtrate was concentrated under reduced pressure to obtain 2-(2-pyrimidinylthio)ethylamine (6.6 g 71%) as an oil.

NMR (δ ppm in CDCl$_3$): 1.61 (2H, s), 3.04 (2H, t, J=6Hz), 3.27 (2H, t, J=6Hz), 6.98 (1H, t, J=5 Hz), 8.52 (2H, d, J=5 Hz).

Reference Examples 28 to 52

According to the same manner as that described in Reference Example 27, the compounds shown in Tables 8 to 11 were obtained as oil.

TABLE 8

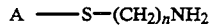

| Ref. Ex. | A— | n | Yield (%) | NMR (δppm in CDCl$_3$) |
|---|---|---|---|---|
| 28 | phenyl | 2 | 87 | 1.57(2H, s), 2.9–3.1(4H, m), 7.2–7.4(5H, m) |
| 29 | phenyl | 3 | 80 | 1.42(2H, s), 1.7–1.9(2H, m), 2.83(2H, t, J=7Hz), 2.99(2H, t, J=7Hz), 7.15–7.4(5H, m) |
| 30 | phenyl | 4 | 99 | 1.29(2H, s), 1.5–1.8(4H, m), 2.71(2H, t, J=7Hz), 2.94(2H, t, J=7Hz), 7.1–7.4(5H, m) |
| 31 | phenyl | 5 | 94 | 1.4–1.8(8H, m), 2.69(2H, t, J=7Hz), 2.93 (2H, t, J=7Hz), 7.1–7.4(5H, m) |

TABLE 8-continued $$\boxed{A} - S-(CH_2)_n NH_2$$

| Ref. Ex. | A | n | Yield (%) | NMR (δppm in CDCl$_3$) |
|---|---|---|---|---|
| 32 | phenyl | 6 | 92 | 1.25–1.75(10H, m), 2.68(2H, t, J=7Hz), 2.92(2H, t, J=7Hz), 7.1–7.4(5H, m) |
| 33 | 4-Cl-phenyl | 4 | 99 | 1.5–1.75(6H, m), 2.71(2H, t, J=7Hz), 2.91 (2H, t, J=7Hz), 7.25(4H, s) |
| 34 | 2-pyridyl | 2 | 75 | 1.63(2H, s), 3.00(2H, t, J=7Hz), 3.29(2H, t, J=7Hz), 6.97(1H, ddd, J=7, 5, 1Hz), 7.19(1H, ddd, J=8, 1, 1Hz), 7.47(1H, ddd, J=8, 7, 2Hz), 8.41(1H, ddd, J=5, 2, 1Hz) |
| 35 | 2-pyridyl | 3 | 82 | 1.57(2H, s), 1.8–1.95(2H, m), 2.83(2H, t, J=7Hz), 3.25(2H, t, J=7Hz), 6.97(1H, ddd, J=7, 5, 1Hz), 7.17(1H, ddd, J=8, 1, 1Hz), 7.47(1H, ddd, J=8, 7, 2Hz), 8.42(1H, ddd, J=5, 2, 1Hz) |

TABLE 9

$$\boxed{A} - S-(CH_2)_n NH_2$$

| Ref. Ex. | A | n | Yield (%) | NMR (δppm in CDCl$_3$) |
|---|---|---|---|---|
| 36 | 2-pyridyl | 4 | 78 | 1.36(2H, s), 1.5–1.85(4H, m), 2.74 (2H, t, J=7Hz), 3.18(2H, t, J=7Hz), 6.97(1H, ddd, J=7, 5, 1Hz), 7.17(1H, ddd, J=8, 1, 1Hz), 7.47 (1H, ddd, J=8, 7, 2Hz), 8.42(1H, ddd, J=5, 2, 1Hz) |
| 37 | 2-pyridyl | 5 | 91 | 1.3–1.65(6H, m), 1.65–1.85(2H, m), 2.69 (2H, t, J=7Hz), 3.17(2H, t, J=7Hz), 6.96(1H, ddd, J=7, 5, 1Hz), 7.16(1H, ddd, J=8, 1, 1Hz), 7.46(1H, ddd, J=8, 7, 2Hz), 8.41(1H, ddd, J=5, 2, 1Hz) |
| 38 | 2-pyridyl | 6 | 95 | 1.3–1.65(8H, m), 1.65–1.8(2H, m), 2.68(2H, t, J=7Hz), 3.16(2H, t, J=7Hz), 6.96(1H, ddd, J=7, 5, 1Hz), 7.16(1H, ddd, J=8, 1, 1Hz), 7.46(1H, ddd, J=8, 7, 2Hz), 8.41(1H, ddd, J=5, 2, 1Hz) |
| 39 | 4-pyridyl | 2 | 94 | 1.6–1.9(2H, broad), 3.0–3.2(4H, m), 7.13 (2H, d, J=6Hz), 8.39(2H, d, J=6Hz) |
| 40 | 4-pyridyl | 3 | 97 | 1.57(2H, s), 1.8–1.95(2H, m), 2.87(2H, t, J=7Hz), 3.06(2H, t, J=7Hz), 7.12(2H, d, J=6Hz), 8.38(2H, d, J=6Hz) |

TABLE 9-continued

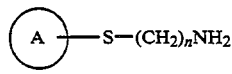
A—S—(CH$_2$)$_n$NH$_2$

| Ref. Ex. | A— | n | Yield (%) | NMR (δppm in CDCl$_3$) |
|---|---|---|---|---|
| 41 | N⌬— (4-pyridyl) | 4 | 99 | 1.50–1.85(6H, m), 2.76(2H, t, J=7Hz), 2.98 (2H, t, J=7Hz), 7.10(2H, d, J=6Hz), 8.37 (2H, d, J=6Hz) |
| 42 | N⌬— (4-pyridyl) | 5 | 90 | 1.4–1.6(6H, m), 1.6–1.8(2H, m), 2.6–2.8 (2H, m), 2.98(2H, t, J=7Hz), 7.10(2H, d, J=6 Hz), 8.38(2H, d, J=6Hz) |

TABLE 10

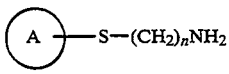
A—S—(CH$_2$)$_n$NH$_2$

| Ref. Ex. | A— | n | Yield (%) | NMR (δppm in CDCl$_3$) |
|---|---|---|---|---|
| 43 | 1-methylimidazol-2-yl | 4 | 89 | 1.57–1.72(6H, m), 2.72(2H, t, J=7Hz), 3.07 (2H, t, J=7Hz), 3.62(3H, s), 6.92(1H, d, J= 1Hz), 7.05(1H, d, J=1Hz) |
| 44 | 1-methylimidazol-2-yl | 2 | 93 | 1.63(2H, s), 2.96(2H, double t, J=6and1 Hz), 3.13(2H, double t, J=6 and 1Hz), 3.64(3H, s), 6.93(1H, d, J=1Hz), 7.05 (1H, d, J=1Hz) |
| 45 | 3-methyl-1,2,4-thiadiazol-5-yl | 4 | 83 | 1.49(2H, s), 1.56–1.67(2H, m), 1.78–1.93 (2H, m), 2.72(3H, s), 2.75(2H, t, J=7Hz), 3.32(2H, t, J=7Hz) |
| 46 | 3-methyl-1,2,4-thiadiazol-5-yl | 2 | 79 | 1.61(2H, s), 2.73(3H, s), 3.10(2H, t, J= 7Hz), 3.40(2H, t, J=6Hz) |
| 47 | pyrimidin-2-yl | 5 | 88 | 1.43–1.53(6H, m), 1.73–1.80(2H, m), 2.71(2H, t, J=7Hz), 3.16(2H, t, J=7Hz), 6.95(1H, t, J=5Hz), 8.51(2H, d, J=5Hz) |
| 48 | pyrimidin-2-yl | 4 | 87 | 1.40(2H, s), 1.57–1.84(4H, m), 2.75(2H, t, J=7Hz), 3.17(2H, t, J=7Hz), 6.95(1H, t, J= 5Hz), 8.51(2H, d, J=5Hz) |
| 49 | pyrimidin-2-yl | 3 | 77 | 1.57(2H, s), 1.9(2H, m), 2.86(2H, t, J=7Hz), 3.23(2H, t, J=7Hz), 6.96(1H, t, J=5Hz), 8.51(2H, d, J=5Hz) |

TABLE 11

$$A \!-\! S\!-\!(CH_2)_n NH_2$$

| Ref. Ex. | 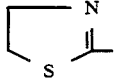 A | n | Yield (%) | NMR (δ ppm in CDCl₃) |
|---|---|---|---|---|
| 50 | 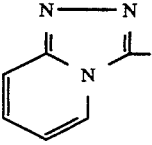 | 4 | 77 | 1.48–1.80(6H, m), 2.72(2H, t, J=7Hz), 3.12 (2H, t, J=7Hz), 3.38(2H, t, 8Hz), 4.21 (2H, t, J=8Hz) |
| 51 | | 4 | 96 | 1.5–2.0(6H, m), 2.72(2H, t, J=7Hz), 3.17(2H, t, 3=7Hz), 6.92(1H, t, J=7Hz), 7.31 (1H, t, J=7Hz), 7.77(1H, d, J=7Hz), 8.12(1H, d, J=7Hz) |
| 52 | 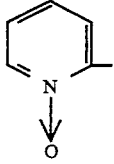 | 4 | 99 | 1.55–1.95(6H, m), 2.77(2H, t, J=7Hz), 2.93(2H, t, J=7Hz), 7.0–7.3(3H, m), 8.27 (1H, ddd, J=5, 2, 1Hz) |

Reference Example 53

According to the same manner as that described in Reference Example 21, N-[4-[(4-methoxyphenyl)thio]butyl]phthalimide was obtained and recrystallized from acetoneisopropyl ether, m.p. 61°–62° C.

Reference Example 54

According to the same manner as that described in Reference Example 1,N-[4-[(2-thiazolyl)thio]butyl]phthalimide was obtained and recrystallized from ethanol, m.p. 60°–61° C.

Reference Example 55

According to the same manner as that described in Reference Example 1, N-[4-[(1-methyl-1, 2, 3, 4-tetrazol-5-yl)thio]butyl]phthalimide was obtained and recrystallized from ethanol, m.p. 92°–93° C.

Reference Example 56

According to the same manner as that described in Reference Example 27, 4-[(4-methoxyphenyl)thio]butylamine was obtained as an oil.

NMR (δ ppm in CDCl₃): 1.50 (2H, s), 1.53–1.88 (4H, m), 2.77 (2H, t, J=7 Hz), 3.77 (3H, s), 3.93 (2H, t, J=7 Hz), 6.83 (4H, s).

Reference Example 57

According to the same manner as that described in Reference Example 27, 4-[(4-methoxyphenyl)thio]butylamine was obtained as an oil.

NMR (δ ppm in CDCl₃): 1.37 (2H, s), 1.52–1.67 (2H, m), 1.82 (2H, m), 2.74 (2H, t, J=7 Hz), 3.24 (2H, t, J=7 Hz), 7.21 (1H, d, J=3 Hz), 7.67 (1H, d, J=3 Hz).

Reference Example 58

According to the same manner as that described in Reference Example 27, 4-[(1-methyl-1,2,3,4-tetrazol-5-yl) thio]butylamine was obtained as an oil.

NMR (δ ppm in CDCl₃): 1.61 (2H, m), 1.69 (2H, s), 1.88 (2H, m), 2.77 (2H, t, J=7 Hz ), 3.37 (2H, t, J=7 Hz ), 3.92 (3H, s).

EXAMPLE 1

4-(Phenylthio)butylamine (7.90 g), ethyl orthoformate (12.9 g) and diethyl phosphite (24.1 g) were stirred overnight at 150° C. The reaction mixture was concentrated under reduced pressure and the residue was subjected to silica gel column chromatography. Tetraethyl 4-(phenylthio)butylaminomethylene bisphosphonate ( 11.1 g, 54%) was obtained as a colorless oil from fraction eluted with chloroform-methanol (50:1, v/v).

NMR (δ in CDCl₃): 1.34 (12H, t, J=7 Hz), 1.50–1.70 (4H, m), 2.85 (2H, t, J=7 Hz), 2.93 (2H, t, J=7 Hz), 3.23 (1H, t, J=22 Hz), 4.12–4.30 (8H, m), 7.10–7.40 (5H, m).

EXAMPLE 2

According to the same manner as that in Example 1, tetraethyl 4-(4-chlorophenylthio)butylaminomethylenebisphosphonate was obtained as a colorless oil starting from 4-(4-chlorophenylthio)butylamine (40%).

NMR δ (CDCl₃): 1.34 (12H, t, J=7 Hz), 1.55–1.70 (4H, m), 2.86 (2H, t, J=7 Hz), 2.90 (2H, t, J=7 Hz), 3.23 (1H, t, J=22 Hz), 4.12–4.29 (8H, m), 7.24 (4H, s).

EXAMPLE 3

According to the same manner as that in Example 1, tetraethyl 3-(phenylthio)propylaminomethylenebisphosphonate was obtained as a colorless oil starting from 3-(phenylthio)propylamine (33%).

NMR δ (CDCl₃): 1.35 (12H, t, J=7 Hz), 1.65–1.80 (2H, m), 2.95 (2H, d, J=7 Hz), 3.01 (2H, d, J=7 Hz), 3.27 (1H, t, J=22 Hz), 4.10–4.30 (8H, m), 7.10–7.40 (5H, m).

EXAMPLE 4

According to the same manner as that in Example 1, tetraethyl 2-(phenylthio)ethylaminomethylenebisphosphonate was obtained as a colorless oil starting from 3-(phenylthio)ethylamine (28%).

NMR δ (CDCl$_3$): 1.33 (12H, t, J=7 Hz), 3.5 (4H, s), 3.27 (1H, t, J=22 Hz), 4.12–4.29 (8H, m), 7.14–7.40 (5H, m).

EXAMPLE 5

Tetraethyl 4-(phenylthio)butylaminomethylenebisphosphonate (11.1 g) was dissolved in concentrated hydrochloric acid (150 ml) and the mixture was refluxed for 2.5 hours. After the reaction mixture was concentrated under reduced pressure, water was poured and separated crystals were collected by filtration to obtain 4-(phenylthio)butylaminomethylenebisphosphonic acid (4.94 g) as a white powder. Sodium methylate (28% methanol solution, 13.3 g) was added to the suspension of this powder (4.08 g) in methanol (50 ml), and the resultant was stirred at room temperature for one hour and then concentrated under reduced pressure. Methanol was added to the residue, the separated white crystals were collected by filtration and recrystallized from water-methanol to obtain tetrasodium 4-(phenylthio)butylaminomethylenebisphosphonate as a white powder ( 3.90 g, 43% ).

Melting Point: >300° C.

Elemental Analysis for C$_{11}$H$_{15}$NO$_6$SP$_2$Na$_4$.H$_2$O, Calcd.: C, 28.65; H, 3.72; N, 3.04 Found: C, 28.50; H, 3.69; N, 2.95

NMR δ (D$_2$O): 1.67–1.86 (4H, m), 2.91 (1H, t, J=17 Hz), 3.06 (2H, t, J=7 Hz), 3.24 (2H, t, J=7 Hz), 7.25–7.50 (5H,m).

EXAMPLE 6

According to the same manner as that in Example 5, tetrasodium 4-(4-chlorophenylthio)butylaminomethylenebisphosphonate (68%, recrystallization solvent: water-MeOH) was obtained as a white powder starting from tetraethyl 4-(4-chlorophenylthio)butylaminomethylenebisphosphonate.

Elemental Analysis for C$_{11}$H$_{14}$ClNO$_6$SP$_2$Na$_4$.½H$_2$O, Calcd.: C, 27.15; H, 3.11; N, 2.88 Found: C, 27.28; H, 3.40; N, 2.94

NMR δ (D$_2$O): 1.65–1.90 (4H, m), 2.90 (1H, t, J=17 Hz), 3.04 (2H, t, J=7 Hz), 3.23 (2H, t, J=7 Hz), 7.39 (4H, s).

EXAMPLE 7

According to the same manner as that in Example 5, tetrasodium 3-(phenylthio) propylaminomethylenebisphosphonate (45%, recrystallization solvent: water-MeOH) was obtained starting from tetraethyl 3-(phenylthio) propylaminomethylenebisphosphonate.

Elemental Analysis for C$_{10}$H$_{13}$NO$_6$SP$_2$Na$_4$.H$_2$O, Calcd.: C, 26.86; H, 3.38; N, 3.13 Found: C, 27.12; H, 3.48; N, 2.97

NMR δ (D$_2$O): 2.00 ( 2H, quintet, J=7 Hz), 2.89 (1H, t, J=17 Hz), 3.10 (2H, d, J=7 Hz ), 3.32 ( 2H, d, J=7 Hz), 7.25–7.55 (5H, m).

Example 8

According to the same manner as that in Example 5, tetrasodium 2-(phenylthio)ethylaminomethylenebisphosphonate as a white powder was obtained starting from tetraethyl 2-(phenylthio)ethylaminomethylenebisphosphonate (43%, recrystallization solvent: water-methanol).

Melting Point: >300° C.

Elemental Analysis for C$_9$H$_{11}$NO$_6$SP$_2$Na$_4$.½H$_2$O, Calcd.: C, 25.48; H, 2.85; N, 3.30 Found: C, 25.37; H, 2.90; N, 3.19

NMR δ (D$_2$O): 2.75 (1H, t, J=17 Hz), 3.24 (4H, s), 7.27–7.57 (5H, m).

Example 9

According to the same manner as that in Example 1, tetraethyl 4-(2-pyridylthio)butylaminomethylenebisphosphonate was obtained as a colorless oil starting from 4-(2-pyridylthio)butylamine (yield: 54%).

NMR δ (CDCl$_3$): 1.34 (12H, t, J=7 Hz), 1.60–1.90 (4H, m), 2.88(2H, t, J=7 Hz), 3.18 (2H, t, J=7 Hz), 3.26 (1H, t, J=22 Hz), 4.10–4.30 (8H, m), 6.96 (1H, ddd, J=7, 5, 1 Hz), 7.16 (1H, d, J=8 Hz), 7.47 (1H, ddd, J=8, 7, 2 Hz), 8.42 (1H, ddd, J=5, 2, 1 Hz).

Example 10

A solution of tetraethyl 4-(2-pyridylthio)butylaminomethylenebisphosphonate (2.50 g) in hydrochloric acid (40 ml) was stirred for 3 hours under reflux. The reaction mixture was concentrated under reduced pressure. Acetone was added to the residue and the separated white precipitate was collected by filtration and recrystallized from water-methanol to obtain 4-(2-pyridylthio)butylaminomethylenebisphosphonic acid hydrochloride (1.46 g, 70%) as a white powder.

Melting Point: 176–178° C.

Elemental Analysis for C$_{10}$H$_{18}$N$_2$O$_6$SP$_2$.HCl, Calcd.: C, 30.58; H, 4.88; N, 7.13 Found: C, 30.59; H, 5.10; N, 7.02

NMR δ (D$_2$O): 1.80–2.00 (4H, m), 3.35–3.47 (4H, m), 3.53 (1H, t, J=17 Hz), 7.70 (1H, dd, J=7, 6 Hz), 7.95 (1H, J=8 Hz), 8.36 (1H, dd, J=8, 7 Hz), 8.53 (1H, d, J=6 Hz).

EXAMPLE 11-31

According to the same manner as that in Example 1, the compounds shown in Tables 12-15 were obtained as oil.

TABLE 12

$$\text{A} - \text{S}-(CH_2)_n-NH-CH\begin{array}{c}P(O)(OC_2H_5)_2\\P(O)(OC_2H_5)_2\end{array}$$

| Ex. No. | A— | n | Reaction temp. (°C.) | Reaction time (hr.) | Yield (%) | NMR (δppm in CDCl₃) |
|---|---|---|---|---|---|---|
| 11 | phenyl | 5 | 150 | 5 | 44 | 1.35(12H, t, J=7Hz), 1.42–1.75(6H, m), 2.83(2H, t, J=7Hz), 2.91(2H, t, J=7Hz), 3.24(1H, t, J=22Hz), 4.10–4.32(8H, m), 7.12–7.36(5H, m) |
| 12 | phenyl | 6 | 150 | 4 | 40 | 1.34(12H, t, J=7Hz), 1.40–1.80(8H, m), 2.91(4H, t, J=7Hz), 3.24(1H, t, J=22Hz), 4.10–4.30(8H, m), 7.10–7.37(5H, m) |
| 13 | 2-pyridyl | 2 | 150 | 2 | 28 | 1.33(12H, t, J=7Hz), 3.15(2H, t, J=7Hz), 3.31(2H, t, J=7Hz), 3.40(1H, t, J=22Hz), 4.11–4.31(8H, m), 6.97(1H, ddd, J=7, 5, 1Hz), 7.17(1H, ddd, J=8, 1, 1Hz), 7.46(1H, ddd, J=8, 7, 2Hz), 8.40(1H, ddd, J=5, 2, 1Hz) |
| 14 | 2-pyridyl | 3 | 150 | 2 | 47 | 1.34(12H, t, J=7Hz), 1.88(2H, quintet, J=7Hz), 3.00(2H, t, J=7Hz) 3.25(2H, t, J=7Hz), 3.31(1H, t, J=22Hz), 4.11–4.31(8H, m), 6.97(1H, ddd, J=7, 5, 1Hz), 7.16(1H, ddd, J=8, 1, 1Hz), 7.47(1H, ddd, J=8, 7, 2Hz) 8.43(1H, ddd, J=5, 2, 1Hz) |
| 15 | 2-pyridyl | 5 | 150 | 3 | 45 | 1.35(12H, t, J=7Hz), 1.45–1.80(6H, m), 2.84(2H, t, J=7Hz), 3.16(2H, t, J=7Hz), 3.24(1H, t, J=22Hz), 4.14–4.30(8H, m), 6.96(1H, ddd, J=7, 5, 1Hz), 7.15(1H, ddd, J=8, 1, 1Hz), 7.46(1H, ddd, J=8, 7, 2Hz), 8.41(1H, ddd, J=5, 2, 1Hz) |

TABLE 13

$$\text{A} - \text{S}-(CH_2)_n-NH-CH\begin{array}{c}P(O)(OC_2H_5)_2\\P(O)(OC_2H_5)_2\end{array}$$

| Ex. No. | A— | n | Reaction temp. (°C.) | Reaction time (hr.) | Yield (%) | NMR (δppm in CDCl₃) |
|---|---|---|---|---|---|---|
| 16 | 2-pyridyl | 6 | 150 | 3 | 27 | 1.35(12H, t, J=7Hz), 1.30–1.80(8H, m), 2.83(2H, t, J=7Hz), 3.16(2H, t, J=7Hz), 3.25(1H, t, J=22Hz), 4.13–4.32(8H, m), 6.97(1H, ddd, J=7, 5, 1 Hz), 7.17(1H, ddd, J=8, 1, 1Hz), 7.47(1H, ddd, J=8, 7, 2Hz), 8.42(1H, ddd, J=5, 2, 1Hz) |
| 17 | 4-pyridyl | 2 | 145 | 2 | 16 | 1.34(12H, t, J=7Hz), 1.95(1H, s), 3.1–3.3(4H, m), 3.29(1H, t, J=22Hz), 4.1–4.3(8H, m), 7.13(2H, d, J=6Hz), 8.39(2H, d, J=6Hz) |
| 18 | 4-pyridyl | 3 | 145 | 2 | 21 | 1.35(12H, t, J=7Hz), 1.7–2.0(3H, m) 2.9–3.2(4H, m), 3.25(1H, t, J=22Hz), 4.1–4.3(8H, m), 7.12(2H, double d, J=6 and 2Hz), 8.38(2H, double d, J=6 and 2Hz) |

TABLE 13-continued $$A—S—(CH_2)_n—NH—CH\begin{matrix}P(O)(OC_2H_5)_2\\P(O)(OC_2H_5)_2\end{matrix}$$

| Ex. No. | A— | n | Reaction temp. (°C.) | Reaction time (hr.) | Yield (%) | NMR (δppm in CDCl₃) |
|---|---|---|---|---|---|---|
| 19 | 4-pyridyl | 4 | 150 | 2 | 10 | 1.34(12H, t, J=7Hz), 1.56–1.86(4H, m), 2.90(2H, t, J=7Hz), 3.00(2H, t, J=7Hz), 3.24(1H, t, J=22Hz), 4.08–4.31(8H, m), 7.11(2H, dd, J=6, 2Hz), 8.39(2H, dd, J=6, 2Hz) |
| 20 | 4-pyridyl | 5 | 140 | 3 | 25 | 1.35(12H, t, J=7Hz), 1.4–1.6(2H, m) 1.6–1.8(2H, m), 1.9–2.2(3H, m), 2.85(2H, t, J=7Hz), 3.00(2H, t, J=7Hz), 3.24(1H, t, J=22Hz), 4.1–4.3 (8H, m), 7.10(2H, d, J=6Hz), 8.38(2H, d, J=6Hz) |

TABLE 14

$$A—S—(CH_2)_n—NH—CH\begin{matrix}P(O)(OC_2H_5)_2\\P(O)(OC_2H_5)_2\end{matrix}$$

| Ex. No. | A— | n | Reaction temp. (°C.) | Reaction time (hr.) | Yield (%) | NMR (δppm in CDCl₃) |
|---|---|---|---|---|---|---|
| 21 | 1-methylimidazol-2-yl | 2 | 140 | 3 | 30 | 1.34(12H, t, J=7Hz), 1.92(1H, s), 3.12–3.21(4H, m), 3.31(1H, t, J=22 Hz), 3.62(3H, s), 4.13–4.29(8H, m) 6.91(1H, d, J=1Hz), 7.03(1H, d, J=1Hz) |
| 22 | 1-methylimidazol-2-yl | 4 | 140 | 3 | 11 | 1.35(12H, t, J=7Hz), 1.63–1.73(4H, m), 1.88(1H, s), 2.85(2H, t, J=7Hz), 3.10(2H, t, J=7Hz), 3.23(1H, t, J=22 Hz), 3.62(3H, s), 4.13–4.28(8H, m), 6.93(1H, d, J=1Hz), 7.07(1H, d, J=1Hz) |
| 23 | 3,5-dimethyl-1,2,4-thiadiazol-yl | 2 | 150 | 3 | 38 | 1.35(12H, t, J=7Hz), 1.79(1H, s), 2.72(3H, s), 3.27(2H, t, J=6Hz), 3.32 (1H, t, J=21Hz), 3.44(2H, t, J=6Hz), 4.14–4.31(8H, m) |
| 24 | 3,5-dimethyl-1,2,4-thiadiazol-yl | 4 | 140 | 3 | 40 | 1.35(12H, t, J=7Hz), 1.59–1.67(2H, m), 1.67(1H, s), 1.82–1.90(2H, m), 2.72(3H, s), 2.88(2H, t, J=7Hz), 3.24 (1H, t, J=22Hz), 3.32(2H, t, J=7Hz), 4.14–4.29(8H, m) |
| 25 | pyrimidin-2-yl | 4 | 140 | 3 | 43 | 1.34(12H, t, J=8Hz), 1.64–1.81(5H, m), 2.90(2H, t, J=7Hz), 3.15(2H, t, J=7Hz), 3.26(1H, t, J=22Hz), 4.13–4.28 (8H, m), 6.95(1H, t, J=5Hz), 8.52(2H, d J=5Hz) |
| 26 | pyrimidin-2-yl | 3 | 140 | 3 | 24 | 1.35(12H, t, J=7Hz), 1.73(1H, s), 1.91(2H, m), 3.00(2H, t, J=7Hz), 3.23 (2H, t, J=7Hz), 3.31(1H, t, J=22Hz), 4.14–4.30(8H, m), 6.95(1H, t, J=5Hz) 8.5(2H, d, J=5Hz) |

TABLE 15

$$A\!-\!\!S\!-\!(CH_2)_n\!-\!NH\!-\!CH\begin{array}{c}P(O)(OC_2H_5)_2\\P(O)(OC_2H_5)_2\end{array}$$

| Ex. No. | A— | n | Reaction temp. (°C.) | Reaction time (hr.) | Yield (%) | NMR (δppm in CDCl₃) |
|---|---|---|---|---|---|---|
| 27 | pyrimidin-yl | 2 | 140 | 3 | 27 | 1.34(12H, t, J=7Hz), 1.69(1H, s), 3.17–3.32(4H, m), 3.40(1H, t, J=22 Hz), 4.14–4.28(8H, m), 6.97(1H, t, J=5Hz), 8.51(2H, d, J=5Hz) |
| 28 | thiazol-yl | 4 | 150 | 3 | 24 | 1.35(12H, t, J=7Hz), 1.57–1.77(5H, m), 2.86(2H, t, J=7Hz), 3.11(2H, t, J=7Hz), 3.24(1H, t, J=22Hz), 3.38(2H, t, J=8Hz), 4.21(2H, t, J=8Hz), 4.14–4.30(8H, m) |
| 29 | pyridyl-N-oxide | 4 | 150 | 5 | 18 | 1.34(12H, t, J=7Hz), 1.5–2.00(4H, m), 2.88(2H, t, J=7Hz), 3.20(1H, t, J=22Hz), 3.22(2H, t, J=7Hz), 4.05–4.30(8H, m), 6.93–7.10(1H, m), 7.16 (1H, dd, J=8 and 1Hz), 7.40–7.46 (1H, m), 8.39–8.45(1H, m) |
| 30 | pyridopyridinyl | 4 | 140 | 3 | 28 | 1.34(12H, t, J=7Hz), 1.5–2.0(5H, m) 2.85(2H, t, J=7Hz), 3.18(2H, t, J=7Hz), 3.23(1H, t, J=22Hz), 4.1–4.3(8H, m), 6.93(1H, t, J=6Hz), 7.25–7.35(1H, m), 7.77(1H, d, J=6Hz), 8.11(1H, d, J=6Hz) |
| 31 | pyrimidinyl | 5 | 150 | 3 | 43 | 1.35(12H, t, J=7Hz), 1.48–1.55(3H, m), 1.67–1.79(4H, m), 2.85(2H, t, J=6Hz), 3.14(2H, t, J=7Hz), 3.25 (1H, t, J=22Hz), 4.14–4.30(8H, m), 6.96(1H, t, J=5Hz), 8.51(2H, d, J=5Hz) |

EXAMPLE 32 m-Chloroperbenzoic acid (487 mg) was added in Small portions to a solution of tetraethyl 4-(phenyl-thio)butylaminomethylenebisphosphonate (1.20 g) in dichloromethane (10 ml) with ice-cooling, and then the mixture was stirred at 0° C. for 2 hours. The reaction mixture was washed successively with aqueous sodium bisulfite, saturated aqueous sodium bicarbonate, and water and then dried (MgSO₄), and concentrated. The residue was chromatographed on silica gel. Tetraethyl 4-(phenylsulfinyl)butylaminomethylenebisphosphonate was obtained as a colorless oil (1.05 g, 85%) from the fraction eluted with chloroformmethanol (50:1, v/v).

NMR (δ ppm in CDCl₃): 1.34 (12H, t, J=7 Hz), 1.45–2.00 (4H, m), 2.82 (2H, t, J=7 Hz), 2.85 (2H, t, J=7 Hz), 3.21 (1H, t, J=22 Hz), 4.08–4.32 (8H, m), 7.48–7.67 (5H, m).

EXAMPLES 33–35

According to the same manner as that in Example 32, the compounds shown in Table 16 were obtained.

TABLE 16

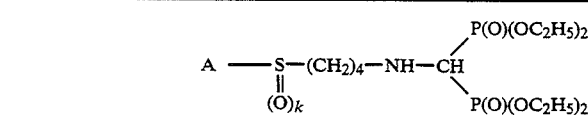

| Ex. No. | A— | k | Yield (%) | NMR (δppm in CDCl₃) |
|---|---|---|---|---|
| 33 | phenyl | 2 | 29 | 1.34(12H, t, J=7Hz), 1.50–1.95(4H, m), 2.84(2H, t, J=7Hz), 3.13(2H, t, J=7Hz), 3.19(1H, t, J=22Hz), 4.08–4.30(8H, m), 7.52–7.74(3H, m), 7.86–7.96(2H, m) |

TABLE 16-continued

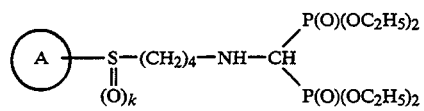

| Ex. No. | ⟨A⟩— | k | Yield (%) | NMR (δppm in CDCl₃) |
|---|---|---|---|---|
| 34 | 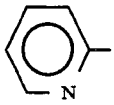 | 1 | 83 | 1.34(12H, t, J=7Hz), 1.50–2.00(4H, m), 2.85(2H, t, J=7Hz), 3.11(2H, t, J=7Hz), 3.22(1H, t, J=22Hz), 4.06–4.29(8H, m), 7.38(1H, ddd, J=7, 5, 1Hz), 7.87–7.99 (2H, m), 8.62(1H, ddd, J=5, 2, 1Hz) |
| 35 | 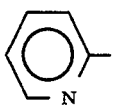 | 2 | 34 | 1.33(12H, t, J=7Hz), 1.50–2.00(4H, m), 2.85(2H, t, J=7Hz), 3.21(1H, t, J=22Hz), 3.43(2H, t, J=7Hz), 4.00–4.30(8H, m), 7.37(1H, ddd, J=7, 5, 1Hz), 7.86–8.04(2H, m), 8.61(1H, ddd, J=5, 2, 1Hz) |

EXAMPLES 36–39

According to the same manner as that in Example 5, the compounds shown in Table 17 were obtained.

TABLE 17

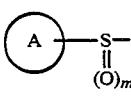

| Ex. No. | ⟨A⟩— | m | n | Yield (%) | m.p. (°C.) | Recrystn. solvent | Molecular formula |
|---|---|---|---|---|---|---|---|
| 36 |  | 1 | 4 | 49 | >300 | water-MeOH | C₁₁H₁₅NO₇P₂SNa₄·2H₂O |
| 37 | 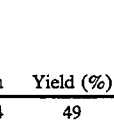 | 2 | 4 | 73 | >300 | water-MeOH | C₁₁H₁₅NO₈P₂SNa₄·H₂O |
| 38 |  | 0 | 5 | 48 | >300 | water-MeOH | C₁₂H₁₇NO₆P₂SNa₄ |
| 39 |  | 0 | 6 | 54 | >300 | water-MeOH | C₁₃H₁₉NO₆P₂SNa₄ |

EXAMPLE 40

Bromotrimethylsilane (1.80 g) was added dropwise to a solution of tetraethyl 4-[(2-pyridine 1-oxide)thio]-butylaminomethylenebisphosphonate (1.14 g) in acetonitrile (20 ml) and the resultant was stirred overnight at room temperature. Water was added to the reaction mixture, and the resultant was further stirred at room temperature for one hour, and then concentrated under reduced pressure. The residue was dissolved in methanol (10 ml), to which was added sodium methoxide (28% methanol solution, 2.72 g), and the resultant was stirred at room temperature for one hour and concentrated under reduced pressure. Acetone was added to the residue and the separated white precipitate was collected by filtration, which was recrystallized from water-methanol to obtain trisodium 4-[(2-pyridine 1-oxide)thio]butylaminomethylenebisphosphonate as a white powder (220 mg, 20%).

Melting Point: >300° C.

Elemental Analysis for C₁₀H₁₅N₂O₇P₂SNa₃·1.5H₂O,
Calcd.: C, 25.82; H, 3.90; N, 6.02 Found: C, 26.16; H, 3.80; N, 5.88

EXAMPLE 41

Bromotrimethylsilane (13.8 g) was added to a solution of tetraethyl 4-(2-pyrimidylthio)butylaminomethylenebisphosphonate (7.0 g) in acetonitrile (70 ml) and the resultant was stirred at room temperature for 15 hours. After water (5 ml) was added, the reaction mixture was concentrated under reduced pressure. A solution of sodium methoxide in methanol (28%, 18.0 g) and ether (100 ml) were added to the residue, and the separated crystals were collected by filtration and recrystallized from water-ethanol to obtain tetrasodium 4-(2-pyrimidylthio)butylaminomethylenebisphonate monohydrate (2.1 g, 30%) as colorless prisms.

Melting Point: >300° C.

Elemental Analysis for $C_9H_{13}N_3O_6P_2SNa_4 \cdot H_2O$, Calcd.: C, 23.34; H, 3.26; N, 9.07 Found: C, 23.69; H, 3.57; N, 8.95

EXAMPLES 42–50

According to the same manner as that in Example 41, the compounds shown in Table 18 were obtained.

TABLE 18

$$\text{A}-\text{S}-(CH_2)_n-NH-CH\begin{matrix}P(O)(ONa)_2\\P(O)(ONa)_2\end{matrix}$$

| Ex. No. | A- | n | Yield (%) | m.p. (°C.) | Recrystn. solvent | Molecular formula |
|---|---|---|---|---|---|---|
| 42 | N-methylpyrazol-5-yl (N=N, N-CH₃) | 4 | 26 | >300 | water-MeOH | $C_9H_{15}N_3O_6P_2SNa_4 \cdot H_2O$ |
| 43 | N-methylpyrazol-5-yl (N=N, N-CH₃) | 2 | 29 | >300 | water-MeOH | $C_7H_{11}N_3O_6P_2SNa_4 \cdot 7H_2O$ |
| 44 | 5-methyl-1,3,4-thiadiazol-2-yl (CH₃-N-N-S) | 4 | 41 | >300 | MeOH-ether | $C_8H_{13}N_3O_6P_2S_2Na_4 \cdot 4H_2O$ |
| 45 | 5-methyl-1,3,4-thiadiazol-2-yl (CH₃-N-N-S) | 2 | 43 | >300 | water-MeOH | $C_6H_9N_3O_6P_2S_2Na_4 \cdot 6H_2O$ |
| 47 | 5-methyl-1,3,4-thiadiazol-2-yl (CH₃-N-N-S) | 5 | 40 | >300 | water-MeOH | $C_{10}H_{15}N_3O_6P_2SNa_4 \cdot H_2O$ |
| 48 | pyrimidin-2-yl | 3 | 23 | >300 | water-MeOH | $C_8H_{11}N_3O_6P_2SNa_4 \cdot 2H_2O$ |
| 49 | pyrimidin-2-yl | 2 | 57 | >300 | water-MeOH | $C_7H_9N_3O_6P_2SNa_4 \cdot 1.5H_2O$ |
| 50 | thiazol-2-yl | 4 | 32 | >300 | water-MeOH | $C_8H_{14}N_2O_6P_2S_2Na_4 \cdot 0.5H_2O$ |

EXAMPLE 51

A mixture of tetraethyl 3-(4-pyridylthio)propylaminomethylenebisphosphonate (7.4 g) and concentrated hydrochloric acid (50 ml) was heated under reflux for 2 hours, and then concentrated under reduced pressure. The residual crystals were collected by filtration to obtain 3-(4-pyridylthio)propylaminomethylenebisphosphonic acid hemihydrate (4.3 g, 77%), and recrystallized from water.

Melting Point: 280°–281° C.
Elemental Analysis for $C_9H_{16}N_2O_6P_2S \cdot \frac{1}{2}H_2O$, Calcd.: C, 30.77; H, 4.87; N, 7.98 Found: C, 30.60; H, 5.09; N, 7.92

EXAMPLES 52–60

According to the same manner as that in Example 51, the compounds shown in Table 19 were obtained.

was stirred at room temperature for 5 hours. The reaction mixture was concentrated under reduced pressure and the residual solid was recrystallized from water-methanol to obtain disodium 5-(2-Pyridylthio)pentylaminomethylenebisphosphonate 1.5 hydrate (0.591 g, 69%).
Melting Point: >300° C.
Elemental Analysis for $C_{11}H_{18}N_2O_6P_2SNa_2 \cdot 1.5H_2O$,

TABLE 19

$$\text{(A)}-S-(CH_2)_n-NH-CH\begin{array}{c}P(O)(OH)_2\\P(O)(OH)_2\end{array}$$
$$\overset{\|}{(O)_m}$$

| Ex. No. | (A)— | m | n | Yield (%) | m.p. (°C.) | Recrystn. solvent | Molecular formula |
|---|---|---|---|---|---|---|---|
| 52 | 2-pyridyl | 0 | 2 | 68 | 252–253 | water-MeOH | $C_8H_{14}N_2O_6P_2S \cdot 0.5H_2O$ |
| 53 | 2-pyridyl | 0 | 3 | 68 | 242–244 | water-MeOH | $C_9H_{16}N_2O_6P_2S \cdot 0.5H_2O$ |
| 54 | 2-pyridyl | 0 | 5 | 66 | 208–210 | water-MeOH | $C_{11}H_{20}N_2O_6P_2S \cdot H_2O$ |
| 55 | 2-pyridyl | 0 | 6 | 61 | 213–214 | water-MeOH | $C_{12}H_{22}N_2O_6P_2S$ |
| 56 | 4-pyridyl | 0 | 2 | 93 | 288–289 | water | $C_8H_{14}N_2O_6P_2S \cdot 0.5H_2O$ |
| 58 | 4-pyridyl | 0 | 5 | 95 | 279–280 | water | $C_{11}H_{20}N_2O_6P_2S \cdot 0.5H_2O$ |
| 59 | imidazo[1,2-a]pyridyl | 0 | 4 | 39 | 222–223 | water | $C_{11}H_{18}N_4O_6P_2S \cdot 0.5H_2O$ |
| 60 | 4-pyridyl | 1 | 4 | 47 | 232–235 | water-MeOH | $C_{10}H_{18}N_2O_7P_2S \cdot 1.5H_2O$ |

EXAMPLE 61

5-(2-Pyridythio)pentylaminomethylenebisphosphonic acid monohydrate (0.75 g) was suspended in methanol (20 ml) and a solution of sodium methoxide in methanol (28%, 1.0 g) was added thereto. The resultant Calcd.: C, 29.94; H, 4.80; N, 6.35 Found: C, 30.05; H, 4.58; N, 6.36

EXAMPLES 62–65

According to the same manner as that in Example 61, the compounds shown in Table 20 were obtained.

TABLE 20

$$\text{A}-\text{S}-(CH_2)_n-NH-CH\begin{smallmatrix}P(O)(OH)(ONa)_2\\P(O)(OH)(ONa)_2\end{smallmatrix}$$

| Ex. No. | A— | n | Yield (%) | m.p. (°C.) | Recrystn. solvent | Molecular formula |
|---|---|---|---|---|---|---|
| 62 | 2-pyridyl | 2 | 77 | >300 | water-MeOH | $C_8H_{12}N_2O_6P_2SNa_2 \cdot 1.5H_2O$ |
| 63 | 2-pyridyl | 3 | 73 | >300 | water-MeOH | $C_9H_{14}N_2O_6P_2SNa_2 \cdot 1.5H_2O$ |
| 65 | 2-pyridyl | 6 | 70 | >300 | water-MeOH | $C_{12}H_{20}N_2O_6P_2SNa_2 \cdot 0.5H_2O$ |

EXAMPLE 66

According to the same manner as that in Example 1, tetraethyl 4-[(4-methoxyphenyl)thio]butylaminomethylenebisphosphonate was obtained as an oil.

NMR (δ ppm in CDCl$_3$): 1.35 (12H, t, J=7 Hz), 1.58–1.90 (4H, m), 2.91 (2H, t, J=7 Hz), 3.27 (12H, t, J=22 Hz), 3.77 (3H, s), 3.91 (2H, t, J=7 Hz), 4.12–4.30 (8H, m), 6.82 (4H, s).

EXAMPLE 67

According to the same manner as that in Example 1, tetraethyl 4-[(2-thiazolyl)thio]butylaminomethylenebisphosphonate was obtained as an oil.

NMR (δ ppm in CDCl$_3$): 1.34 (12H, t, J=7 Hz), 1.58–1.69 (3H, m), 1.76–1.87 (2H, m), 2.88 (2H, t, J=7 Hz), 3.23 (2H, t, J=7 Hz), 3.24 (1H, t, J=22 Hz), 4.13–4.29 (8H, m), 7.21 (1H, d, J=3 Hz), 7.66 (1H, d, J=3 Hz).

Example 68

According to the same manner as that in Example 1, tetraethyl 4-[(1-methyl-1, 2, 3, 4-tetrazol-5-yl)thio]butylaminomethylenebisphosphonate was obtained as an oil NMR (δ ppm in CDCl$_3$): 1.35 (12H, t, J=7 Hz), 1.59–1.93 (5H, m), 2.89 (2H, t, J=7 Hz), 3.24 (1H, t, j=22 Hz), 3.38 (2H, t, J=7 Hz), 3.92 (3H, s), 4.14–4.31 (8H, m).

EXAMPLE 69

According to the same manner as that in Example 55, 4-[(4-methoxyphenyl)thio]butylaminomethylenebisphosphonic acid was obtained, m.p. 188°–189° C.

Elemental analysis for $C_{12}H_{21}NO_7P_2S \cdot H_2O$, Calcd.: C, 37.22; H, 5.99; N, 3.62 Found: C, 36.99; H, 6.19; N, 3.74

Example 70

According to the same manner as that in Example 61, disodium 4-[(4-methoxyphenyl)thio]butylaminomethylenebisphosphonate was obtained and recrystallized from water-methanol, m.p. >300° C.

Elemental analysis for $C_{12}H_{19}NO_7P_2SNa_2 \cdot 2H_2O$, Calcd.: C, 32.08; H, 5.16; N, 3.12 Found: C, 32.05; H, 5.06; N, 3.26

EXAMPLE 71

To a solution of tetraethyl 4-[(2-thiazolyl)thio]butylaminomethylenebisphosphonate (6.34 g) in acetonitrile (100 ml) was added bromotrimethylsilane (12.27 g) and the mixture was stirred at room temperature for 15 hours. Water (3.3 ml) was added to the reaction mixture and the mixture was concentrated under reduced pressure. The residue was suspended in methanol (50 ml) and sodium methylate (28% methanol solution, 15.5 ml) was added thereto. The mixture was treated with ether (150 ml), and the separated solid was filtered off and recrystallized from water-methanol to obtain disodium 4-[(2-thiazolyl)thio]butylaminomethylenebisphosphonate (3.36 g), m.p. >300° C.

Elemental analysis for $C_8H_{14}N_2O_6P_2S_2Na_2 \cdot 2.5H_2O$, Calcd.: C, 21.29; H, 4.24; N, 6.21 Found: C, 21.11; H, 4.42; N, 6.08

EXAMPLE 72

According to the same manner as that in Example 40, tetrasodium 4-[(1-methyl-1, 2, 3, 4-tetrazol-5-yl)thio]butylaminomethylenebisphosphonate was obtained and recrystallized from water-methanol, m.p. >300° C.

Elemental analysis for $C_7H_{15}N_2O_7P_2Na_4$, Calcd.: C, 18.00; H, 3.24; N, 14.99 Found: C, 18.25; H, 3.62; N, 14.70

Example 73

According to the same manner as that in Example 10, 4-[(2-pyridyl)sulfinyl]butylaminomethylenebisphosphonic acid was obtained and recrystallized from water-ethanol, m.p. 235–240° C.

Elemental analysis for $C_{10}H_{18}N_2O_7P_2S\cdot H_2O$, Calcd.: C, 30.77; H, 5.17; N, 6.67 Found: C, 30.87; H, 5.28; N, 6.79

EXAMPLE 74

To a solution of tetraethyl 4-(phenylthio)-butylaminomethylenebisphosphonate (2.5 g) in ethanol (20 ml) was added a solution of sodium hydroxide (450 mg) in ethanol (20 ml). The mixture was heated under reflux for 4 hours and concentrated under reduced pressure. The residue was dissolved in water and the solution was subjected to column chromatography on Amberlite CG-50 (H+form) and eluted with water to obtain diethyl 4-(phenylthio)butylaminomethylenebisphosphonate monosodium salt (810 mg). The resultant was recrystallized from methanol-hexane, m.p. 143°–145° C.

NMR ($\delta$ ppm in $D_2O$): 1.27 (6H, t, J=7 Hz), 1.65–1.95 (4H, m), 3.05 (2H, t, J=7 Hz), 3.3–3.4 (2H, m), 3.46 (1H, t, J=18.5 Hz), 3.9–4.1 (4H, m), 7.25–7.5 (5H, m).

Elemental analysis for $C_{15}H_{26}NO_6P_2SNa\cdot\frac{1}{2}H_2O$, Calcd.: C, 40.73; H, 6.15; N, 3.17 Found: C, 40.70; H, 6.18; N, 3.25

EXAMPLE 75

To a solution of tetraethyl 4-(phenylthio)-butylaminomethylenebisphosphonate (1.0 g) in acetonitrile (10 ml) was added bromotrimethylsilane (0.98 g) and the mixture was stirred at room temperature for 2 days. Water was added to the reaction mixture and concentrated under reduced pressure. The residual solid was filtered off and recrystallized from $H_2O$—$CH_3OH$ to obtain ethyl 4-(phenylthio)butylaminomethylene-bisphosphonate (3.36 g), m.p. 189°–190° C.

NMR ($\delta$ ppm in $d_6$-DMSO): 1.17 (3H, t, J=7 Hz), 1.5–1.9 (4H, m), 2.96 (2H, t, J=7 Hz), 3.16 (2H, broad t, J=7 Hz), 3.36 (1H, t, J=18 Hz), 3.8–4.0 (2H, m), 7.1–7.3 (5H, m), 7.48 (3H, broad s).

Elemental analysis for $C_{13}H_{23}NO_6P_2S\cdot\frac{1}{2}H_2O$, Calcd.: C, 39.80; H, 6.17; N, 3.57 Found: C, 39.93; H, 6.00; N, 3.66

Example 76

Ethyl 4-(phenylthio)butylaminomethylenebisphosphonate hemihydrate (0.2 g) was dissolved in 1N NaOH (0.5 ml) and pH of the solution was adjusted to 7 with 1N NaOH. The solution was subjected to column chromatography on a Amberlite CG-50 (H+form) column and eluted with water to obtain ethyl 4-(phenylthio)-butylaminomethylenebisphosphate monosodium salt (120 mg). The resultant was recrystallized from water-ethanol, m.p. 167°–169° C.

NMR ($\delta$ ppm in $D_2O$): 1.26 (3H, t, J=7 Hz) 1.65–2.0 (4H, m), 3.05 (2H, t, J=7 Hz), 3.3–3.45 (2H, m), 3.47 (1H, t, J=18 Hz), 3.9–4.1 (4H, m), 7.25–7.5 (5H, m).

Elemental analysis for $C_{13}H_{22}NO_6P_2SNa\cdot\frac{1}{2}H_2O$, Calcd.: C, 37.69; H, 5.60; N, 3.38 Found: C, 37.31; H, 5.48; N, 3.41

What is claimed is:

1. A bisphosphonic acid derivative of the general formula

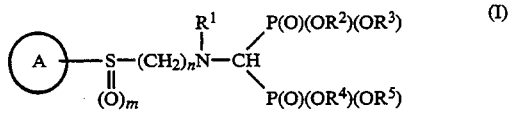

wherein A is a pyridyl group which is unsubstituted or optionally substituted with 1 to 4 substituents selected from the group consisting of (1) a halogen atom, (2) nitro, (3) a $C_{1-7}$ alkyl which may be substituted with 1 to 3 substituents selected from the group consisting of a halogen atom, hydroxy and a $C_{1-6}$ alkoxy, (4) a $C_{3-7}$ cycloalkyl which may be substituted with 1 to 3 substituents selected from the group consisting of a halogen atom, hydroxy and a $C_{1-6}$ alkoxy, (5) a hydroxyl, (6) a protected hydroxyl group selected from the group consisting of $C_{1-6}$ alkoxy, $C_{4-6}$ cycloalkoxy, $C_{2-6}$ alkenyloxy, $C_{6-19}$ aralkyloxy, $C_{2-7}$ alkanoyloxy and $C_{6-14}$ aryloxy, each of which may be substituted with 1 to 3 substituents selected from the group consisting of a halogen, hydroxyl and a $C_{1-6}$ alkoxy, (7) thiol and (8) a protected thiol group selected from the group consisting of a $C_{1-6}$ alkylthio, a $C_{4-7}$ cycloalkylthio, a $C_{7-19}$ aralkylthio and a $C_{2-7}$ alkanolythio, each of which may be substituted with 1 to 3 substituents selected from the group consisting of a halogen, hydroxyl and a $C_{1-6}$ alkoxy; $R^1$ is hydrogen atom or a lower alkanoyl group; $R^2$, $R^3$, $R^4$ and $R^5$ are the same or different and are hydrogen atom or a lower alkyl group; m is 0, 1 or 2; and n is an integer from 2 to 10, or a salt thereof.

2. A compound according to claim 1, wherein the lower alkanoyl represented by $R^1$ is $C_{1-6}$ alkyl-carbonyl group.

3. A compound according to claim 1, wherein the lower alkyl represented by $R^2$, $R^3$, $R^4$ and $R^5$ is $C_{1-4}$ alkyl.

4. A compound which is 4-(2-pyridylthio)-butylaminomethylenebisphosphonic acid, or its salt or $C_{1-4}$ alkyl ester.

5. A compound which is 4-(2-pyridylthio)-butylaminomethylenebisphosphonic acid.

6. A bone resorption inhibitory composition which comprises an effective amount of a compound of the general formula (I) or a salt thereof according to claim 1, and a pharmaceutically acceptable carrier, diluent or excipient.

7. A method of inhibiting bone resorption comprising administering an effective amount of a compound of the formula (I) or a salt thereof according to claim 1, optionally together with a pharmaceutically acceptable carrier, diluent or excipient, to a patient suffering from osteoporosis.

* * * * *